United States Patent
Yoshimi

(12) 
(10) Patent No.: US 11,913,899 B2
(45) Date of Patent: Feb. 27, 2024

(54) SENSOR USING PARTICLES COATED WITH MOLECULARLY IMPRINTED POLYMER

(71) Applicant: SHIBAURA INSTITUTE OF TECHNOLOGY, Tokyo (JP)

(72) Inventor: Yasuo Yoshimi, Tokyo (JP)

(73) Assignee: SHIBAURA INSTITUTE OF TECHNOLOGY, Tokyo (JP)

(*) Notice: Subject to any disclaimer, the term of this patent is extended or adjusted under 35 U.S.C. 154(b) by 554 days.

(21) Appl. No.: 16/471,230

(22) PCT Filed: Dec. 19, 2017

(86) PCT No.: PCT/JP2017/045426
§ 371 (c)(1),
(2) Date: Jun. 19, 2019

(87) PCT Pub. No.: WO2018/117067
PCT Pub. Date: Jun. 28, 2018

(65) Prior Publication Data
US 2021/0278361 A1    Sep. 9, 2021

(30) Foreign Application Priority Data

Dec. 20, 2016 (JP) .................. 2016-246166
Jun. 23, 2017 (JP) .................. 2017-122776
Aug. 7, 2017 (JP) .................. 2017-152349

(51) Int. Cl.
*G01N 27/327* (2006.01)
*C08F 222/38* (2006.01)
(Continued)

(52) U.S. Cl.
CPC ..... *G01N 27/3275* (2013.01); *C08F 222/385* (2013.01); *C08F 292/00* (2013.01); *G01N 33/49* (2013.01)

(58) Field of Classification Search
CPC ........................................ G01N 27/327–3278
(Continued)

(56) References Cited

U.S. PATENT DOCUMENTS

2010/0039124 A1  2/2010  Belbruno et al.
2011/0021347 A1  1/2011  Ugajin et al.
(Continued)

FOREIGN PATENT DOCUMENTS

JP    2009-47507    3/2009
JP    2010-112872   5/2010
(Continued)

OTHER PUBLICATIONS

Xue et al., Amperometric detection of dopamine in human serum by electrochemical sensor based on gold nanoparticles doped molecular imprinted polymers, Biosensors and Bioelectronics, 49, 2013, 199-203 (Year: 2013).*

(Continued)

*Primary Examiner* — Bach T Dinh
(74) *Attorney, Agent, or Firm* — GREENBLUM & BERNSTEIN, P.L.C.

(57) ABSTRACT

An object of the present invention is to provide a sensor in which a molecularly imprinted polymer is immobilized on the surface, the sensor having homogeneous performance and excellent reproducibility of measurement. The present invention provides a sensor comprising: a conductive particle having a molecularly imprinted polymer on the surface; and a support.

13 Claims, 12 Drawing Sheets

(51) Int. Cl.
C08F 292/00 (2006.01)
G01N 33/49 (2006.01)

(58) Field of Classification Search
USPC ..... 204/403.01–403.15; 205/777.5–778, 792
See application file for complete search history.

(56) References Cited

U.S. PATENT DOCUMENTS

| | | | |
|---|---|---|---|
| 2012/0045838 | A1 | 2/2012 | Krozer et al. |
| 2018/0117564 | A1* | 5/2018 | Gluckman ............... B01J 45/00 |
| 2019/0120863 | A1* | 4/2019 | Belbruno ............... G01N 33/94 |

FOREIGN PATENT DOCUMENTS

| | | | |
|---|---|---|---|
| JP | 2010-520477 | | 6/2010 |
| JP | WO2012124800 | * | 9/2012 |
| JP | 2014-504738 | | 2/2014 |
| JP | 2017-150865 | | 8/2017 |
| WO | 2008/107651 | | 9/2008 |
| WO | 2009/028661 | | 3/2009 |
| WO | 2012/104870 | | 8/2012 |
| WO | 2012/124800 | | 9/2012 |
| WO | 2016/140337 | | 9/2016 |

OTHER PUBLICATIONS

Ahmad et al., Nanocomposites of Gold Nanoparticles@Molecularly Imprinted Polymers: Chemistry, Processing, and Applications in Sensors, Chem. Mater., 2015, 27, 5464-5478 (Year: 2015).*
Matsui et al, SPR Sensor Chip for Detection of Small Molecules Using Molecularly Imprinted Polymer with Embedded Gold Nanoparticles, Anal. Chem., 2005, 77, 4282-4285 (Year: 2005).*
Xue et al., Electrochemical serotonin sensing interface based on double-layered membrane of reduced graphene oxide/polyaniline nanocomposites and molecularly imprinted polymers embedded with gold nanoparticles, Sensors and Actuators B, 196, 2014, 57-63 (Year: 2014).*
WO2012124800 machine English translation (Year: 2012).*
Mao et al. Electrochemical sensor for dopamine based on a novel graphene-molecular imprinted polymers composite recognition element, Biosensors and Bioelectronics, 28, 2011, 291-297 (Year: 2011).*
Walach, Molecularly imprinted hydrogels for application in aqueous environment, Polym. Bull., 70, 2013, 70:1647-1657 (Year: 2013).*
Sharma et al., Surface development of molecularly imprinted polymer films to enhance sensing signals, Tends in Analytical Chemistry, 51, 2013, 146-157 (Year: 2013).*
Gholivand et al., Determination of Lamotrigine by Using Molecularly Imprinted Polymer-Carbon Paste Electrode, 2013, Journal of Electroanalytical Chemistry, 692, 9-16 (Year: 2013).*
Svancara et al., Graphtie Powder and Related Material as the Principle Components of Carbon Paste Electrodes, 2013, Graphite, Nova Science Publishers, ISBN: 978-1-62618-576-0 (Year: 2013).*
Office Action issued in the corresponding Indian patent application No. 201947029120, dated Aug. 31, 2021.
Jun Matsui et al., "SPR Sensor CHip for Detection of Small Molecules Using Molecularly Imprinted Polymer with Embedded Gold Nanopariticles", Anal, Chem., 2005, pp. 4282-4285.
International Search Repost issued in International Patent Application No. PCT/JP2017/045426, dated Apr. 3, 2018.
International Preliminary Report on Patentability issued with respect to Patent Application No. PCT/JP2017/045426, dated Jun. 25, 2019 (with English translation).
Office Action issued in corresponding Japanese patent application No. 2018-557986, dated Mar. 30, 2021 with English Machine Translation.

* cited by examiner

[Fig. 1]
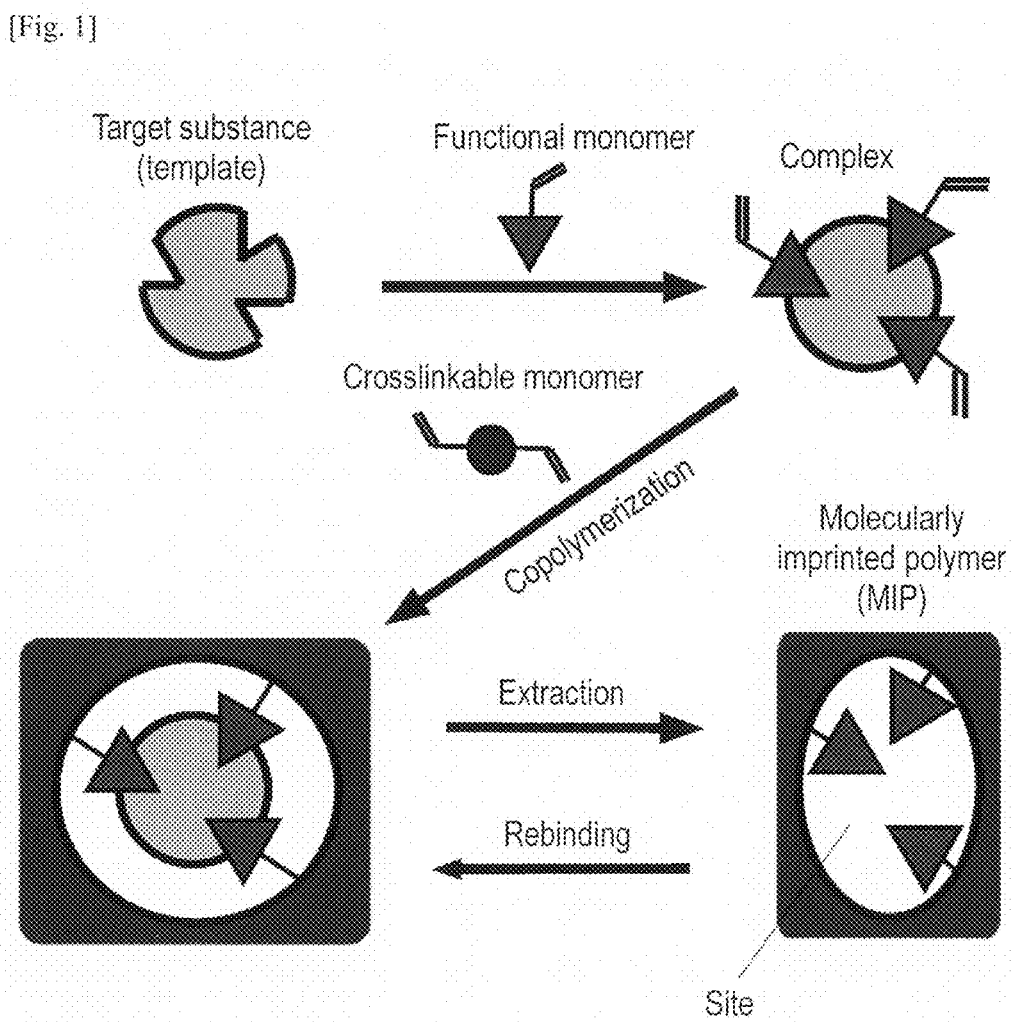

[Fig. 2]
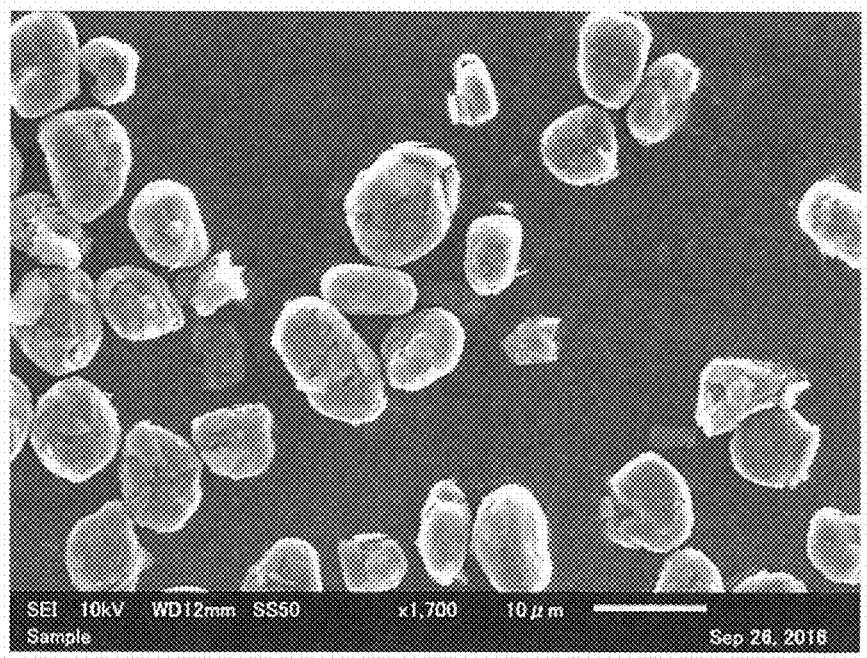
[Fig. 3]
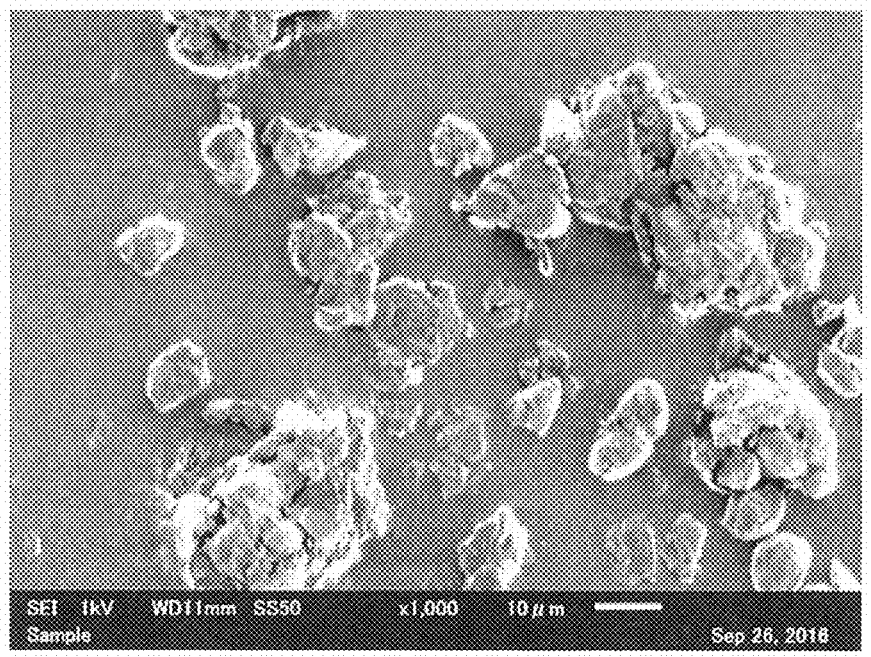

[Fig. 4]
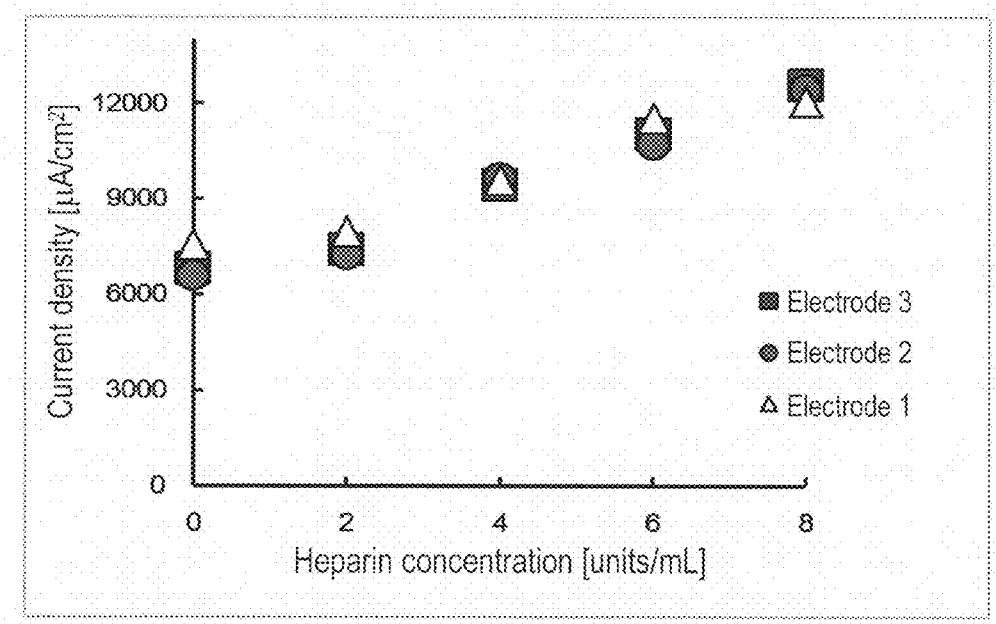
[Fig. 5]
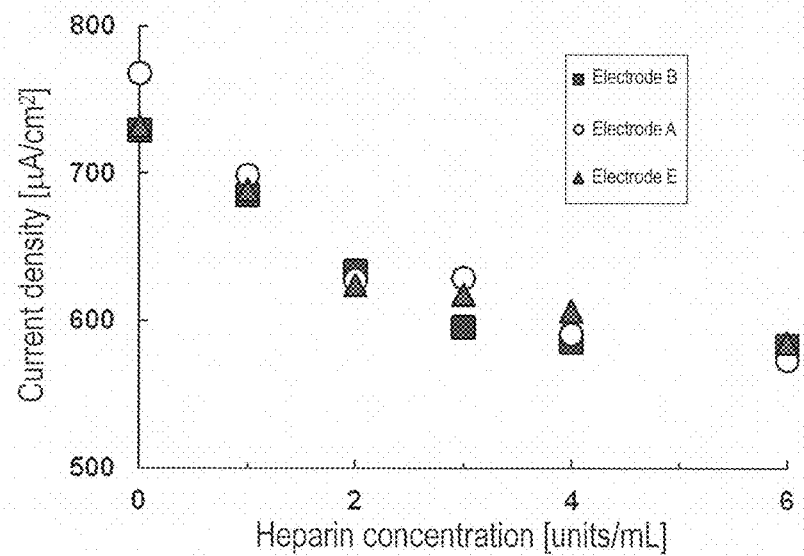

[Fig. 6]
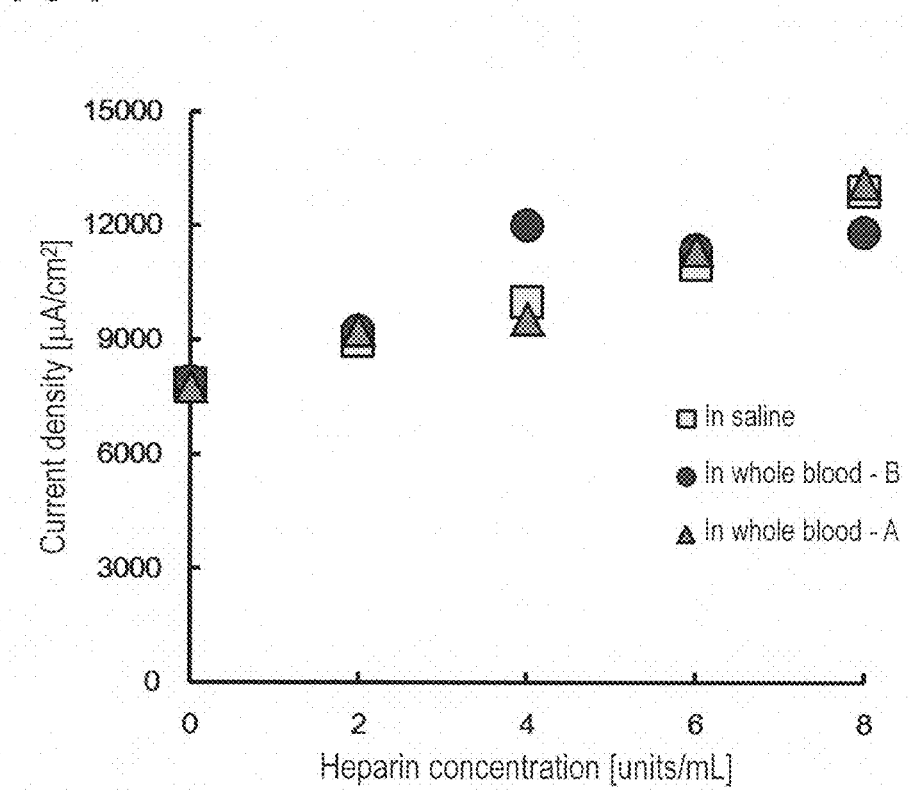
[Fig. 7]
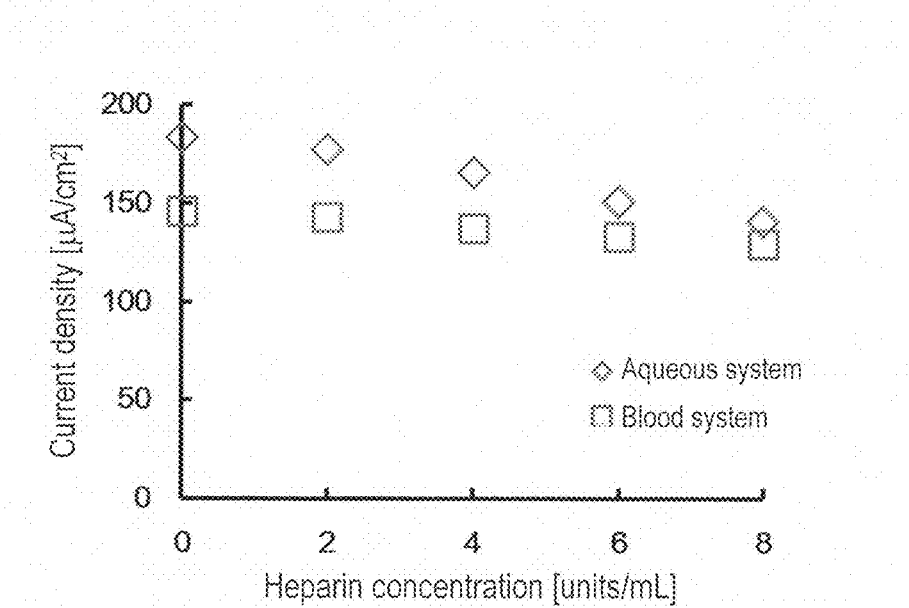

[Fig. 8]
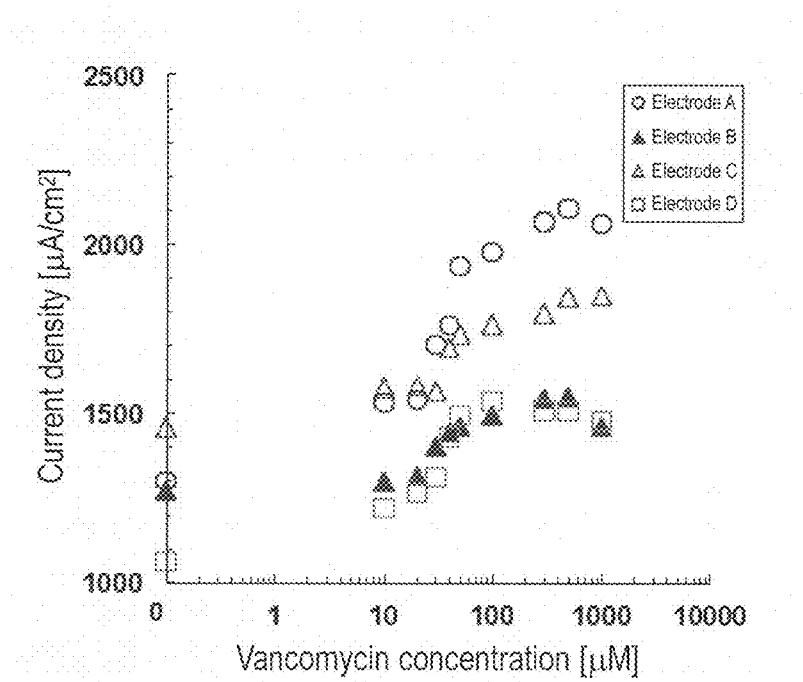
[Fig. 9]
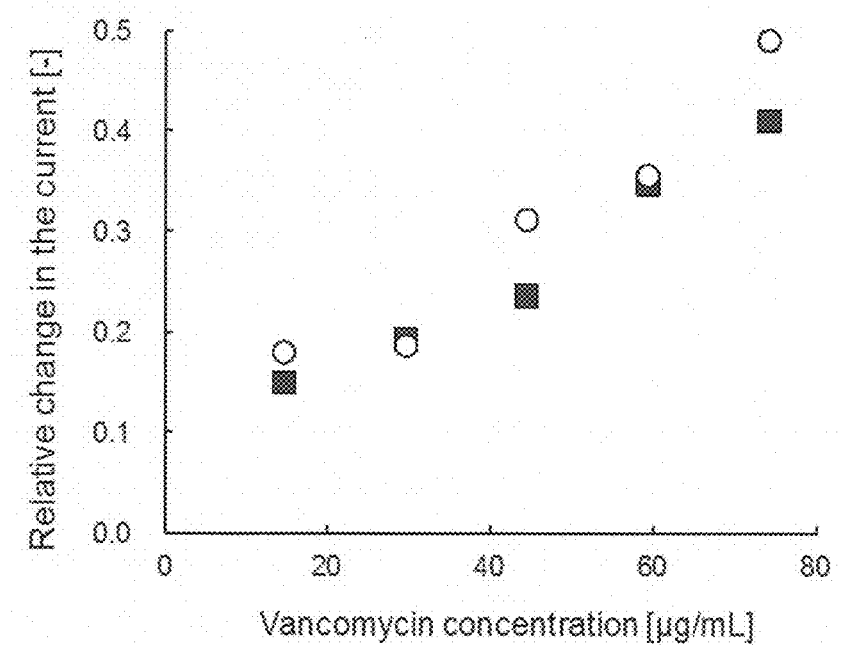

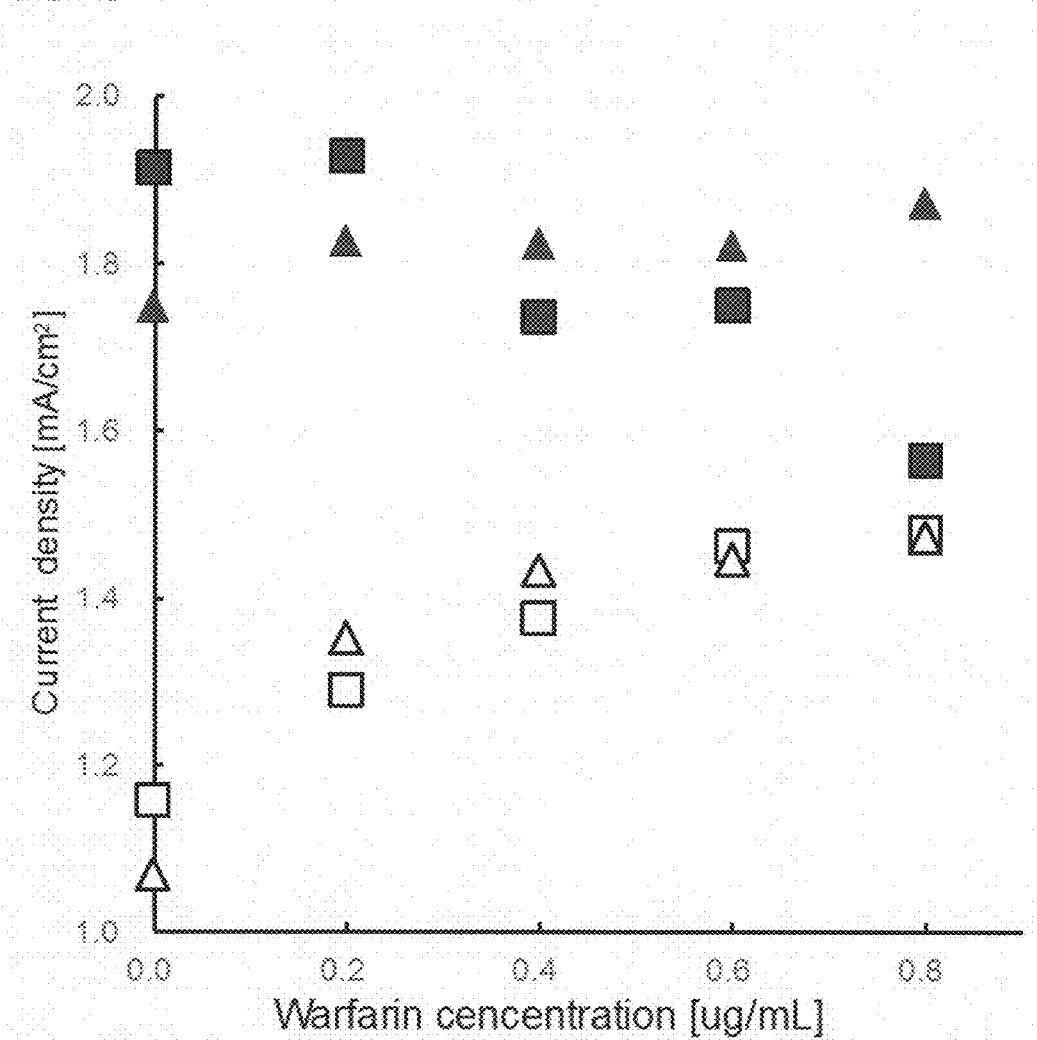
[Fig. 10]

[Fig. 11]
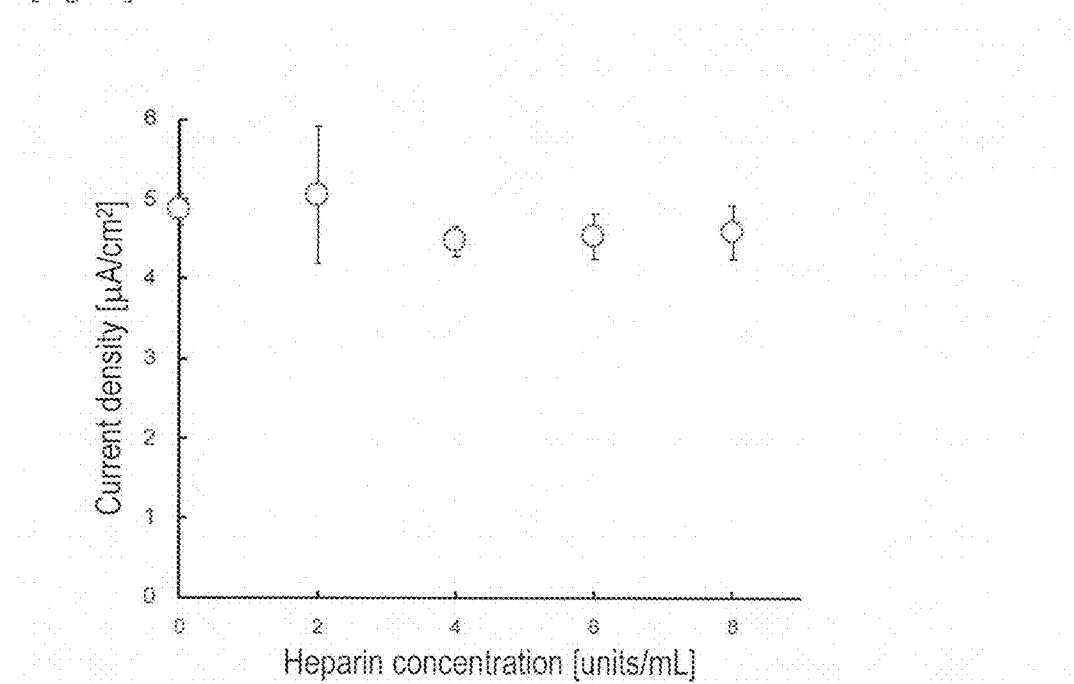
[Fig. 12]
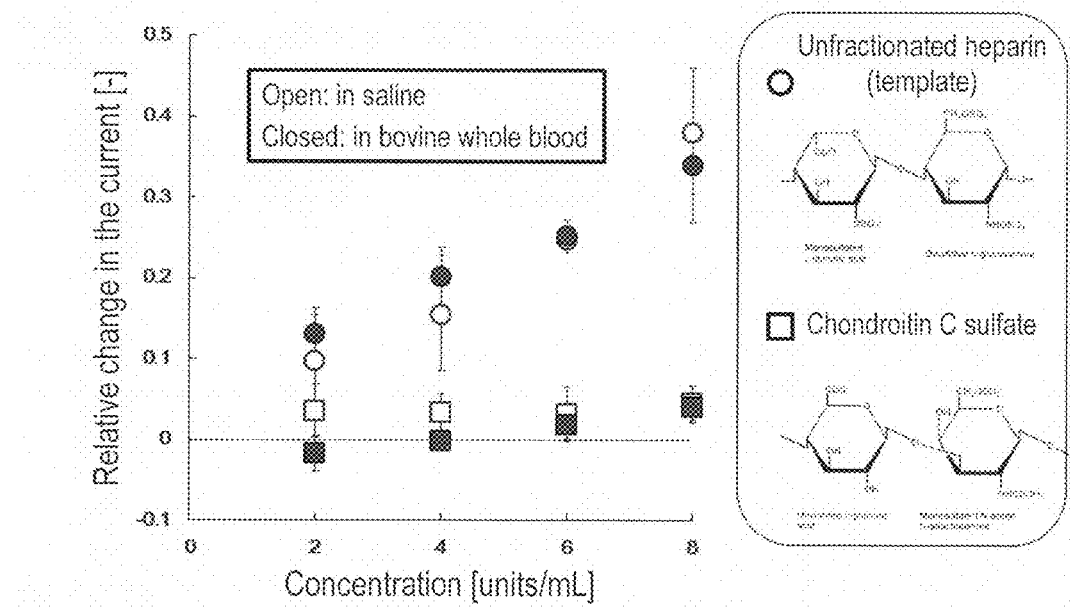

[Fig. 13]
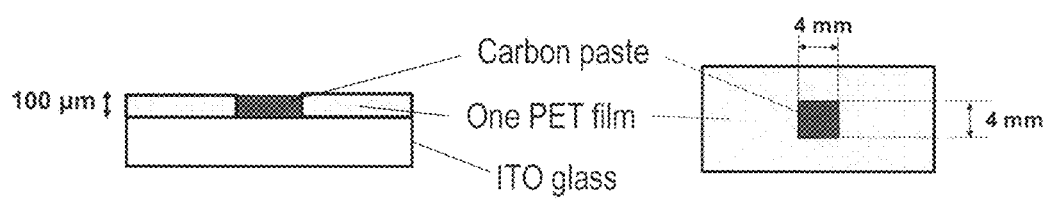
[Fig. 14]
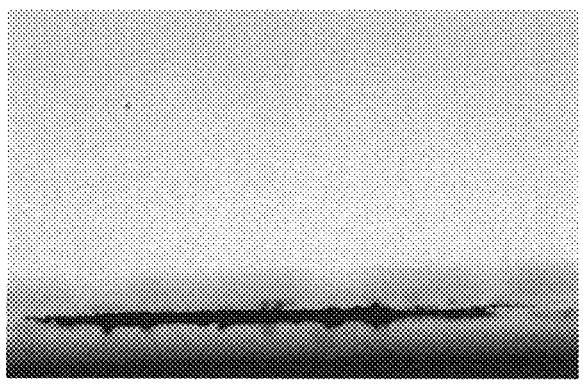
[Fig. 15]
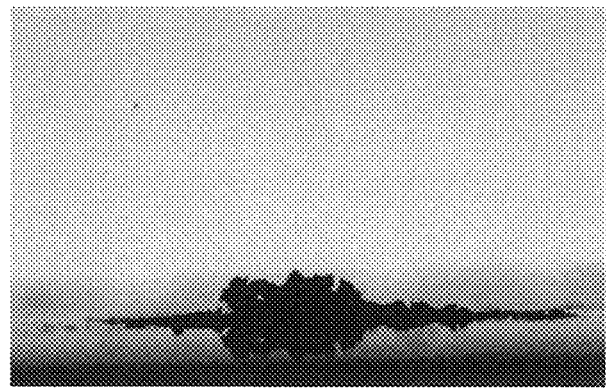

[Fig. 16]
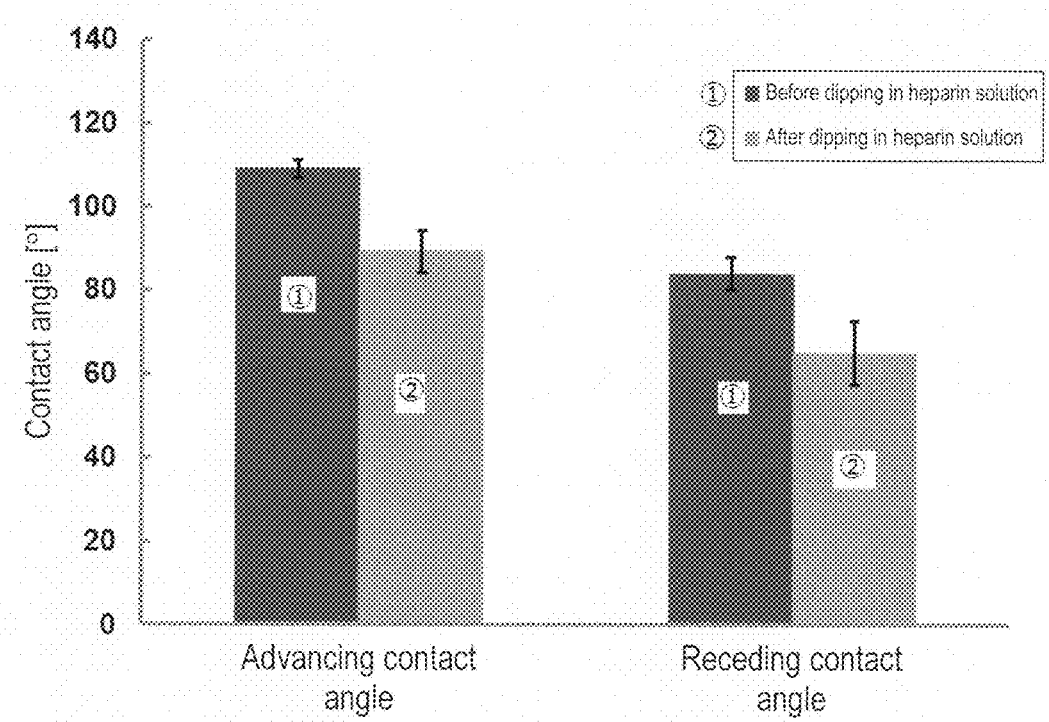
[Fig. 17]
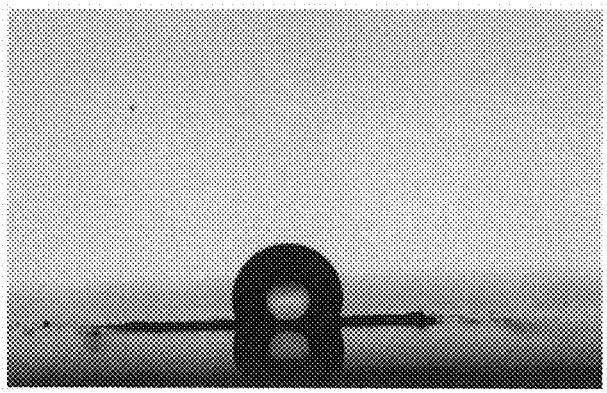

[Fig. 18]
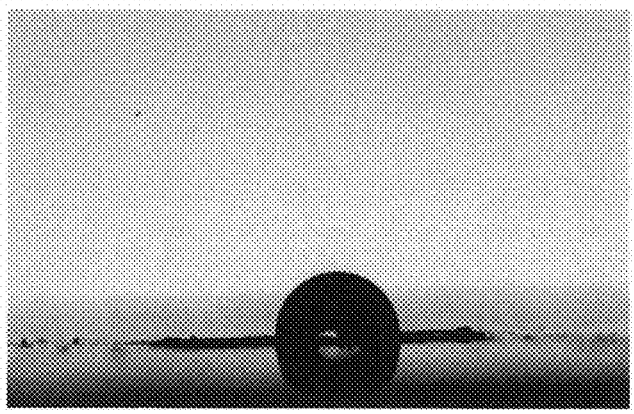
[Fig. 19]
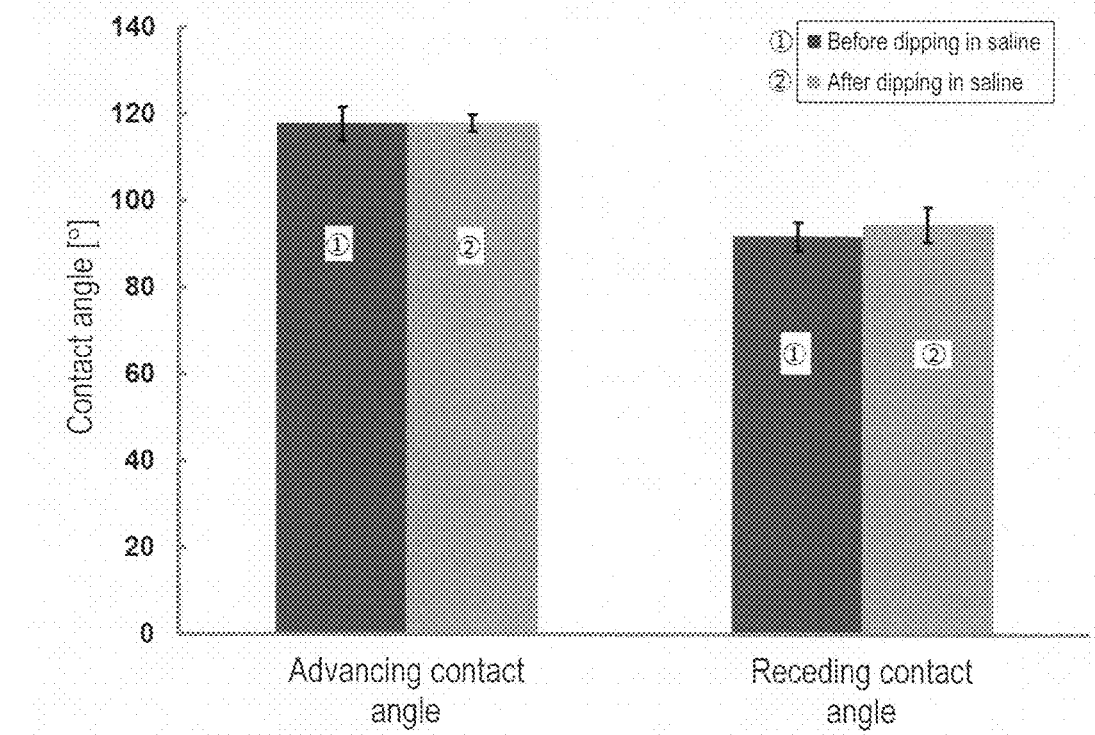

[Fig. 20]
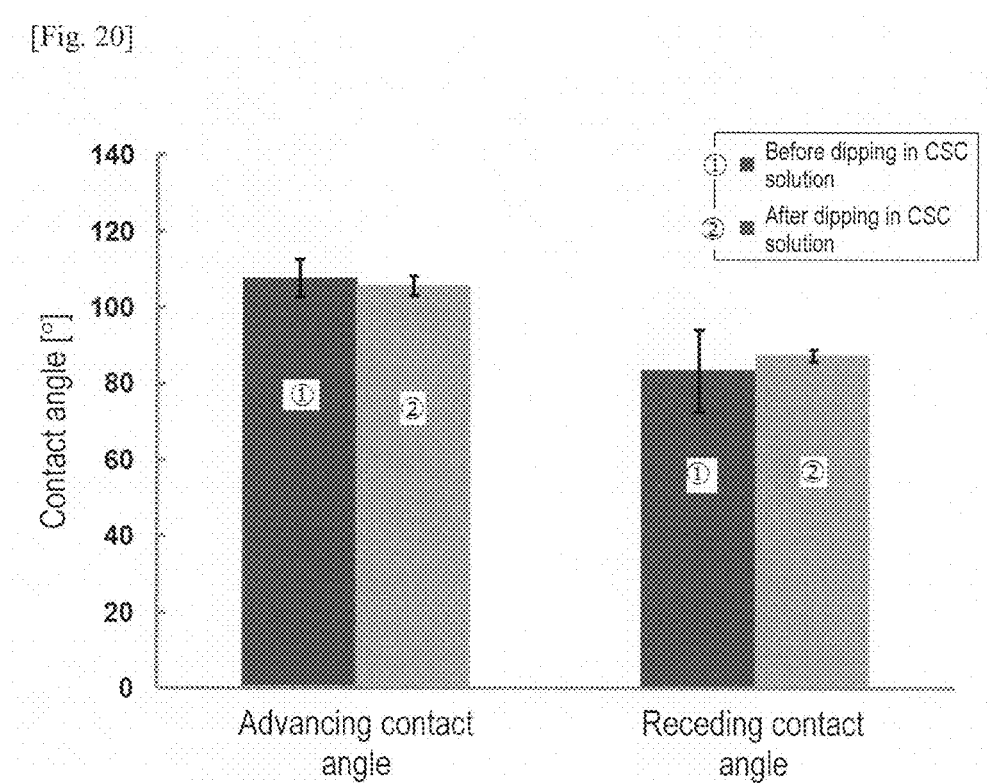
[Fig. 21]
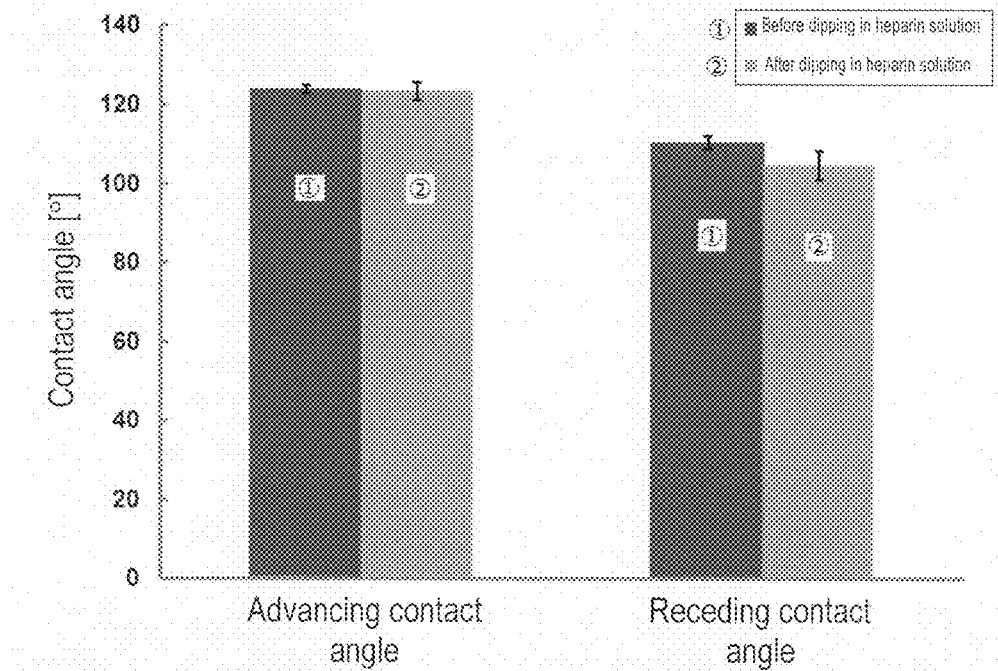

[Fig. 22]
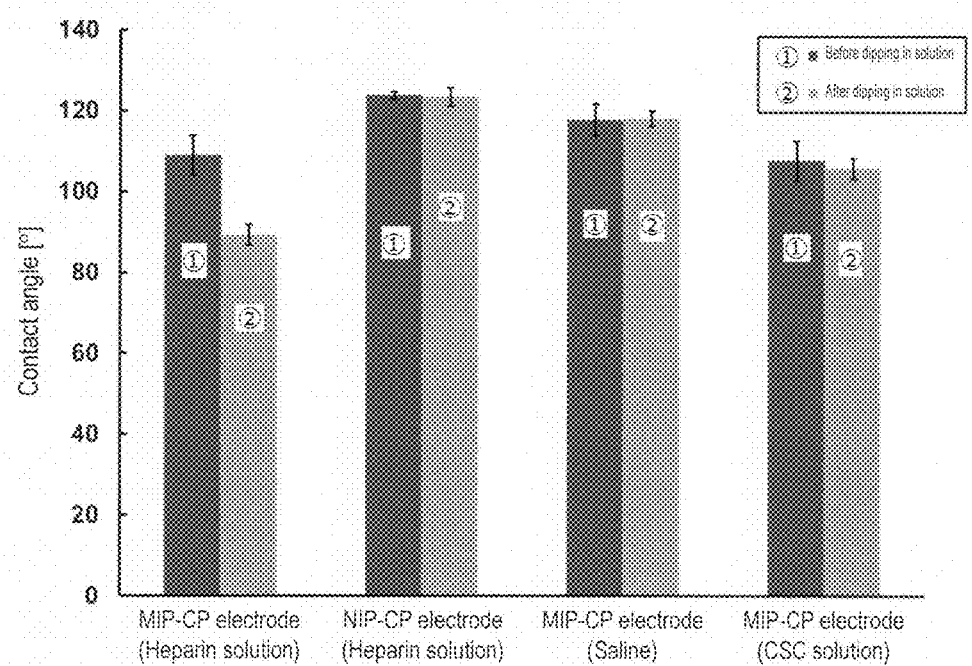
[Fig. 23]
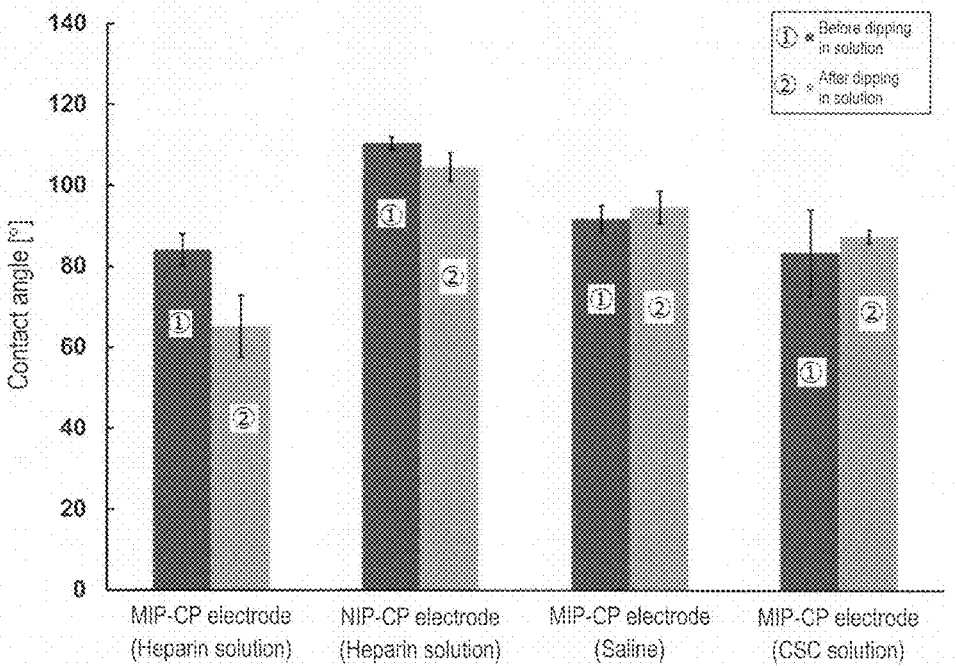

SENSOR USING PARTICLES COATED WITH MOLECULARLY IMPRINTED POLYMER

TECHNICAL FIELD

The present invention relates to a sensor comprising particles coated with layers of molecularly imprinted polymer on the surface, and a measurement method using the sensor.

BACKGROUND ART

For effectively using a therapeutic drug having a strong adverse reaction, therapeutic drug monitoring (TDM) is required in order to confirm that the concentration is sufficient for effective therapy without having toxic effects. However, a proper sensing technique is absent, and thus, TDM has not yet been popular in clinical scenes.

A molecularly imprinted polymer (MIP) is a molecular recognition element obtained by copolymerizing, in the presence of a substance to be recognized (template), a monomer having affinity with the template (functional monomer) and a crosslinkable monomer. This molecular recognition element can be prepared in a tailor-made manner for an arbitrary substance to be recognized by a convenient and economical process. The present inventor has found that redox current in an electrode in which MIP is grafted on the surface depends on the concentration of a template. This is presumably because the specific interaction between the template and MIP causes change in the accessibility of a redox species to a substrate electrode (gate effect). The template can be sensed conveniently and rapidly by measuring this current. On the basis of this finding, Patent Document 1 describes a sensor for anticoagulant measurement comprising a molecularly imprinted polymer-immobilized substrate. Also, Patent Document 2 describes a sensor comprising a substrate in which a molecularly imprinted polymer is directly immobilized on the surface, wherein a redox species is immobilized on the molecularly imprinted polymer and/or the substrate.

PRIOR ART DOCUMENTS

Patent Documents

Patent Document 1: International Publication No. WO2012/124800
Patent Document 2: International Publication No. WO2016/140337

SUMMARY OF INVENTION

Object to be Solved by the Invention

The techniques of Patent Documents 1 and 2 adopt a method which involves grafting MIP by the ultraviolet irradiation of polymerization initiator-immobilized ITO in a solution containing each monomer and a template. Attempts have been made to reduce variations among electrodes to be prepared by thinning a liquid layer large for an electrode or strengthening an irradiation intensity light source in the course of polymerization. However, it has been difficult to secure reproducibility that meets single use. This is presumably because, unfortunately, it is difficult to obtain a homogeneous product by radical polymerization.

An object of the present invention is to overcome the problems described above. In other words, an object of the present invention is to provide a sensor in which a molecularly imprinted polymer is immobilized on the surface, the sensor having homogeneous performance and excellent reproducibility of measurement. Another object of the present invention is to provide a highly sensitive sensor.

Means for Solving the Object

As a result of intensive studies in order to achieve the above objects, the present inventor completed the present invention by preparing a sensor comprising a conductive particle having a molecularly imprinted polymer on the surface, and a support, and confirming its selective response to heparin by cyclic voltammetry.

Specifically, aspects of the present invention relate to the following.

(1) A sensor comprising: a conductive particle having a molecularly imprinted polymer on the surface; and a support.
(2) The sensor according to (1), wherein the conductive particle is a graphite particle.
(3) The sensor according to (1) or (2), wherein the conductive particle having a molecularly imprinted polymer on the surface is a conductive particle obtained by polymerizing a functional monomer, a crosslinkable monomer, and a measurement substance through contact with an initiator-immobilized particle.
(4) The sensor according to (3), wherein the functional monomer is a cationic monomer.
(5) The sensor according to (3) or (4), wherein the functional monomer is trimethylammonium ethyl methacrylate chloride.
(6) The sensor according to any one of (3) to (5), wherein the crosslinkable monomer is methylenebisacrylamide.
(7) The sensor according to any one of (3) to (6), wherein for the polymerization, a monomer for adjustment of the degree of crosslinking is further contacted with the substrate.
(8) The sensor according to (7), wherein the monomer for adjustment of the degree of crosslinking is acrylamide.
(9) The sensor according to any one of (1) to (8), wherein the measurement substance is a hormone, an antimicrobial agent, or an anticoagulant.
(10) The sensor according to any one of (1) to (9), wherein the measurement substance is heparins, warfarin, serotonin, or vancomycin.
(11) A method for measuring a measurement substance, comprising: contacting a sample containing the measurement substance with a sensor according to any one of (1) to (10); and detecting change in signal.
(12) The method for measuring a measurement substance according to (11), comprising detecting change in current as the change in signal.
(13) The measurement method according to (11) or (12), wherein the sample is whole blood or a blood component.

Advantageous Effects of Invention

According to the sensor of the present invention, measurement can be performed with homogeneous performance of the sensor and excellent reproducibility. Furthermore, the sensor of the present invention can exert stable performance both in whole blood and in water solubility. Moreover, the conductive particle having a molecularly imprinted polymer on the surface, used in the present invention can be prepared in a paste state and can therefore be applied to a wide range of supports without particular limitations by the type or form of the support. In addition, according to the sensor of the present invention, more highly sensitive measurement than ever can be performed because of large change in the current density ascribable to change in the concentration of a measurement substance.

BRIEF DESCRIPTION OF DRAWINGS

FIG. 1 shows the principles of molecular imprint.

FIG. 2 shows a SEM image of the surface of an electrode prepared with a conductive particle unmodified with MIP.

FIG. 3 shows a SEM image of the surface of an electrode prepared with a conductive particle modified with MIP.

FIG. 4 shows a heparin concentration and change in the current density when the sensor of the present invention was used.

FIG. 5 shows a heparin concentration and change in the current density when a sensor of a conventional technique was used.

FIG. 6 shows a heparin concentration and change in the current density in whole blood (bovine blood) and in saline when the sensor of the present invention was used.

FIG. 7 shows a heparin concentration and change in the current density in whole blood (bovine blood) and in saline when a sensor of a conventional technique was used.

FIG. 8 shows a vancomycin concentration and change in the current density when the sensor of the present invention was used.

FIG. 9 shows relative change in the current, ascribable to vancomycin addition, of two different vancomycin MIP-immobilized carbon paste electrodes.

FIG. 10 shows the relationship between the peak oxidation current of a ferrocyanide ion and a warfarin concentration in warfarin MIP-immobilized carbon paste electrodes (open: two electrodes differing in lot) or non-imprinted polymer-immobilized carbon paste electrodes (filled: two electrodes differing in lot).

FIG. 11 shows the heparin concentration dependence of current in a non-imprinted polymer (NIP)-grafted paste electrode.

FIG. 12 shows the relationship between an unfractionated heparin concentration and relative change in the current, and the relationship between a chondroitin C sulfate concentration and relative change in the current in bovine whole blood and in saline as to a MIP carbon paste electrode.

FIG. 13 shows a side elevational view (left) and a plane view (right) of a flattened electrode.

FIG. 14 shows the surface, before liquid droplet addition, of a flattened form of carbon grafted with MIP without involving an oil.

FIG. 15 shows the surface of the form after the liquid droplet addition.

FIG. 16 shows change in the hydrophilicity of a MIP-CP electrode between before and after dipping in a heparin solution.

FIG. 17 shows a liquid droplet on the surface of a flattened MIP carbon paste electrode before dipping in a heparin solution.

FIG. 18 shows a liquid droplet on the surface of a flattened MIP carbon paste electrode after dipping in a heparin solution.

FIG. 19 shows the hydrophilicity of a MIP-CP electrode before and after dipping in saline.

FIG. 20 shows change in the hydrophilicity of a MIP-CP electrode between before and after dipping in a CSC solution.

FIG. 21 shows change in the hydrophilicity of a NIP-CP electrode between before and after dipping in a heparin solution.

FIG. 22 shows the comparison of an advancing contact angle.

FIG. 23 shows the comparison of a receding contact angle.

EMBODIMENT OF CARRYING OUT THE INVENTION

Embodiments of the present invention are explained below.

The sensor of the present invention is a sensor comprising: a conductive particle having a molecularly imprinted polymer on the surface; and a support.

A functional monomer and a crosslinkable monomer are copolymerized in a state where a particular substance (template) and the functional monomer which reversibly binds thereto, are self-assembled, so that the molecular structure of the template can be memorized to synthesize a molecularly imprinted polymer which specifically rebinds the template (FIG. 1). This molecularly imprinted polymer is rich in chemical and physical stability and can be prepared at a low cost and in a short time, as compared with a biopolymer. For use of the molecularly imprinted polymer as an element for sensors, it is necessary to generate a signal such as an electric signal appropriate for specific binding to the template. However, since this method had not been established, the application of the molecularly imprinted polymer to a biosensor had not been advanced. The present inventor found that specific reaction with the template changes the size of pores inside a thin film of the molecularly imprinted polymer and furthermore, remarkably changes the permeation rate of a solute in the thin film of the molecularly imprinted polymer (J. Chem. Eng. Jpn., 34, 1466-1469, 2001), and named this phenomenon as a gate effect.

In the present invention, a conductive particle having a molecularly imprinted polymer on the surface is used. The type of the conductive particle is not particularly limited, and a graphite particle, a carbon black particle, a titanium oxide particle, a tin oxide particle, or the like can be used. The particle size of the conductive particle is not particularly limited and is generally 1 μm to 100 μm, preferably 3 μm to 50 μm, more preferably 3 μm to 20 μm, particularly preferably 3 μm to 10 μm.

The conductive particle having a molecularly imprinted polymer on the surface can be produced by polymerizing a functional monomer, a crosslinkable monomer, and a measurement substance through contact with an initiator-immobilized particle. The conductive particle having a molecularly imprinted polymer on the surface can be produced, for example, by immobilizing an initiator (photopolymerization initiator, etc.) onto conductive particles, and dispersing the initiator-immobilized conductive particles in a solution for polymerization containing a functional monomer, a monomer for adjustment of the degree of crosslinking, a crosslinkable monomer and a target for analysis (template), followed by photopolymerization.

The functional monomer used in the present invention is not particularly limited, and acrylic acid, methacrylic acid, itaconic acid, vinylphenylboronic acid, acrylamidoboronic acid, 2-acrylamido-2-methylpropanesulfonic acid, 2-(trifluoromethyl)acrylic acid, or the like can be used. Also, for producing a sensor for heparin measurement, it is preferred to use a cationic monomer. Since heparin contains a large number of sulfonic acid groups, use of such a cationic functional monomer enables synthesis of a molecularly imprinted polymer which specifically binds to heparin. The cationic monomer is a monomer having a cationic group in the molecule, such as primary to tertiary amino group-containing (meth)acrylamide, primary to tertiary amino group-containing (meth)acrylate, quaternary ammonium base-containing (meth)acrylamide, quaternary ammonium base-containing (meth)acrylate, or diallyl dialkylammonium halide. Examples of the tertiary amino group-containing (meth)acrylamide include dimethylaminoethyl(meth)acrylamide, dim ethylaminopropyl(meth)acrylamide, diethylaminoethyl(meth)acrylamide, diethylaminopropyl(meth)acrylamide, and dialkylaminoalkyl(meth)acrylamide. Examples of the tertiary amino group-containing (meth)acrylate include dimethylaminoethyl (meth)acrylate, dimethylaminopropyl (meth)acrylate, diethylaminoethyl (meth)acrylate, diethylaminopropyl (meth)acrylate, and dialkylaminoalkyl (meth)acrylate. Examples of the primary or secondary amino group-containing (meth)acrylamide include primary amino group-containing (meth)acrylamide such as aminoethyl(meth)acrylamide, and secondary amino group-containing (meth)acrylamide such as methylaminoethyl(meth)acrylamide, ethylaminoethyl(meth)acrylamide, and t-butylaminoethyl(meth)acrylamide. Examples of the primary or secondary amino group-containing (meth)acrylate include primary amino group-containing (meth)acrylate such as aminoethyl (meth)acrylate, and secondary amino group-containing (meth)acrylate such as methylaminoethyl (meth)acrylate, ethylaminoethyl (meth)acrylate, and t-butylaminoethyl (meth)acrylate. Examples of the quaternary ammonium base-containing (meth)acrylamide and the quaternary ammonium base-containing (meth)acrylate include mono-quaternary base-containing monomers obtained by quaternizing tertiary amino group-containing (meth)acrylamide or tertiary amino group-containing (meth)acrylate with a quaternizing agent such as methyl chloride, benzyl chloride, methyl sulfate, or epichlorohydrin. Specific examples thereof include acrylamidopropyl trimethylammonium chloride, acrylamidopropylbenzyl dimethyl ammonium chloride, methacryloyloxyethyldimethylbenzylammonium chloride, acryloyloxyethyldimethylbenzylammonium chloride, (meth)acryloyl amino ethyltrimethylammonium chloride, (meth)acryloyl amino ethyltriethylammonium chloride, (meth)acryloyloxyethyltrimethylammonium chloride, and (meth)acryloyloxyethyltriethylammonium chloride. Among those described above, specific examples of the cationic monomer include trimethylammonium ethyl methacrylate chloride, vinylpyridine, and diethylaminoethyl methacrylate. These cationic monomers may be used alone or in combination of two or more.

Examples of the crosslinkable monomer used in the present invention include methylenebisacrylamide, 1,4-butyl diacrylate, 1,6-hexanediol dimethacrylate, polyethylene glycol dimethacrylate, tetraethylene glycol dimethacrylate, ethylene glycol dimethacrylate, diethylene glycol dimethacrylate, triethylene glycol dimethacrylate, nonaethylene glycol dimethacrylate, divinylbenzene, polypropylene glycol dimethacrylate, neopentyl glycol dimethacrylate, pentaerythritol dimethacrylate, trimethylolpropane trimethacrylate, pentaerythritol trimethacrylate, pentaerythritol tetramethacrylate, dipentaerythritol hexamethacrylate, epoxy acrylate, polyester acrylate, and urethane acrylate. Among those described above, for example, methylenebisacrylamide or polyethylene glycol dimethacrylate is particularly preferred. These crosslinkable monomers may be used alone or in combination of two or more.

For the polymerization, a monomer for adjustment of the degree of crosslinking can be used. Acrylamide or the like can be used as the monomer for adjustment of the degree of crosslinking. These monomers for adjustment of the degree of crosslinking may be used alone or in combination of two or more.

The measurement substance to be measured using the sensor of the present invention is not particularly limited, and an arbitrary substance such as a hormone (serotonin, dopamine, adrenaline, acetylcholine, γ-aminobutyric acid, etc.), an antimicrobial agent (vancomycin, teicoplanin, etc.), an anticoagulant, an anesthetic, an agrichemical, or an anticancer agent (gefitinib, fluorouracil, methotrexate, etc.) can be measured.

Examples of the anticoagulant can include, but are not particularly limited to, heparin, heparinoid (including low-molecular-weight heparin and the like), warfarin, acenocoumarol, and phenindione. Heparin used in Examples of the present specification is unfractionated heparin having a molecular weight range of 7000 to 25000 (mostly 10000 to 20000). In the present invention, not only the unfractionated heparin but low-molecular-weight heparin (molecular weight: 4000 to 8000) can be to be measured.

A mechanical prosthetic valve is excellent in durability, and may be semipermanently used once indwelled in the body. Also, a ventricular assist device now exhibits a therapeutic effect comparable to transplantation. However, both the artificial materials are in contact with blood over a long period and are therefore in a state that facilitates coagulating blood. When blood is coagulated, clots clog capillary vessels of the brain or the like, bringing certain death. For preventing this blood coagulation, it is essential to administer an anticoagulant to a patient having a mechanical prosthetic valve or a ventricular assist device. However, most of such patients go about their daily life out of hospitals. Therefore, it is difficult to administer an anticoagulant, such as heparin, which requires injection, to the patients, and an oral anticoagulant is mainly administered thereto. Warfarin, a vitamin K antagonist, is most frequently used as the oral anticoagulant. The overdosing of the anticoagulant is responsible for hemorrhage (particularly, intracerebral hemorrhage). Furthermore, the anticoagulant ability of warfarin is easily influenced by an external factor such as the ingestion of food rich in vitamin K (Natto (fermented soybeans), parsley, etc.). Therefore, dosage design based on the monitoring of the anticoagulant ability is necessary. The monitoring of the anticoagulant ability of warfarin involves adding calcium and thromboplastin to plasma, measuring a coagulation time (prothrombin time), and calculating a relative value (international normalized ratio) by comparison with a normal value, or adopts a method of measuring reduction in the function of a vitamin K-dependent coagulation factor (Thrombotest). Both the approaches are excellent as methods for evaluating the ability to coagulate blood. However, since the anticoagulant ability of warfarin is strongly influenced by an external factor, as mentioned above, results of the prothrombin time or the Thrombotest do not always directly indicate excess or deficiency of the concentration of warfarin. The intestinal absorption rate or metabolism rate of warfarin differs largely among individuals and also varies largely depending on an internal or external factor such as a health condition. Therefore, therapeutic drug monitoring (TDM) is originally required in which dosage design is made while change in the warfarin concentration in blood is monitored. However, a method for selectively measuring warfarin in blood is limited, at present, to a method that requires a large-scale apparatus, such as liquid chromatography with tandem mass spectrometry as a detection method (LC-MS/MS). Such an analysis method is not realistic for frequently measuring a warfarin concentration in blood. There is a demand for the development of a sensor for warfarin that can be operated conveniently at a low cost.

The antimicrobial agent vancomycin is a therapeutic drug of the first choice for gram-positive bacterial infections. The overdosing of this vancomycin causes an adverse reaction such as deafness or renal damage, whereas the underdosing thereof for fear of the adverse reaction not only exerts no therapeutic effect but promotes the appearance of resistant bacteria. Hence, vancomycin is reportedly a typical example of a drug whose concentration in blood needs to be monitored (therapeutic drug monitoring). However, facilities other than major hospitals outsource the quantification of vancomycin in blood to inspection institutes, at present. Therefore, unfortunately, the dose of vancomycin cannot be adjusted at real time. There is a demand for a convenient vancomycin sensor as usable bedside.

The sensor of the present invention may be an electrochemical sensor or may be a non-electrochemical sensor. The electrochemical sensor can be configured by using a molecularly imprinted polymer-immobilized electrode as a molecularly imprinted polymer-immobilized substrate. Alternatively, the non-electrochemical sensor can be configured as a surface plasmon resonance (SPR) sensor (e.g., BIACORE), a quartz crystal microbalance (QCM) sensor, or the like.

One example of the present invention provides a heparin sensor for the electrochemical measurement of heparin. A template sodium heparin, a functional monomer trimethylammonium ethyl methacrylate chloride, and a hydrophilic monomer acrylamide were dissolved in water, and a crosslinkable monomer methylenebisacrylamide was dissolved in an organic solvent dimethylformamide. Both the solutions are mixed to prepare a metastable solution, which can be used in the synthesis of a molecularly imprinted polymer. A radical polymerization initiator is immobilized in advance onto conductive particles through a covalent bond, and the resulting conductive particles can be dispersed in the metastable solution described above, and irradiated with light for graft polymerization to produce conductive particles having a molecularly imprinted polymer on the surface.

The thus-produced conductive particles having a molecularly imprinted polymer on the surface can be applied to the surface of a support (insulating support) by a printing technique or the like to produce a MIP-immobilized electrode having homogeneous surface. A tube may be filled with the conductive particles having a molecularly imprinted polymer on the surface to prepare a MIP electrode.

According to the present invention, a measurement substance can be measured by contacting a sample containing the measurement substance with the sensor described above, and detecting change in signal (preferably change in current). Whole blood or a blood component (e.g., plasma or serum) can be used as the sample.

In the case of using the molecularly imprinted immobilized electrode of the present invention as a sensor, a method can be adopted which involves dipping the electrode, together with a counter electrode and a reference electrode, in a testing solution supplemented with a mediator (redox marker, etc.) such as potassium ferricyanide, potassium ferrocyanide, benzoquinone, or hydroquinone, applying a potential thereto, and measuring the resulting redox current. Uric acid or ascorbic acid present in the body as well as glucose, lactic acid, bilirubin, cholesterol, or the like can be used as the mediator (redox marker, etc.). Alternatively, oxidoreductase (e.g., glucose oxidase, lactate oxidase, cholesterol oxidase, bilirubin oxidase, glucose dehydrogenase, and lactate dehydrogenase) may be used. Uric acid or ascorbic acid itself in the body, when used as the mediator, can be measured directly from perfused blood and therefore enables low invasive measurement without bleeding. The sensor of the present invention can be attached to an apparatus for extracorporeal circulation. The measurement substance in blood can also be measured, for example, by contacting perfused blood with the sensor of the present invention, and detecting change.

The present invention is further specifically explained with reference to the Examples below; however, the present invention is not limited to the Examples.

EXAMPLES

Example 1

(1) Immobilization of Initiator onto Graphite Particle

A dimethyldithiocarbamylmethylene group was introduced as a photo radical polymerization initiator to the surface of graphite particles.

First, a chloromethyl group was introduced to the graphite surface using hydrogen chloride and formaldehyde. A three-neck flask was charged with 5 g of spherical graphite particles (SG-BHB, Ito Graphite Co., Ltd.) having a particle diameter of 8 μm was added, together with a mixed solution of 65 g of concentrated hydrochloric acid and 65 g of acetic acid containing 0.25 g of zinc chloride dissolved therein. The mixture was bubbled with argon gas for 1 hour with vigorous stirring using a magnetic stirrer while cooled in ice. Next, 19.0 g of an aqueous formaldehyde (37.0%) solution was added into this flask, and the mixture was continuously stirred for 4 hours under ice cooling while bubbled with hydrogen chloride gas. Next, the supply of hydrogen chloride was stopped, and the mixture was stirred at room temperature for 6 hours. The particles were washed with 700 mL of distilled water and 200 mL of methanol in this order in a suction filter and dried in vacuum.

The chloromethylated graphite particles were dissolved in 50 mL of a 0.3 M solution of sodium dimethyldithiocarbamate in ethanol and stirred at room temperature for 24 hours to introduce thereto a dimethyldithiocarbamylmethylene group having an initiator function through sodium chloride removal and condensation. The particles were washed with 700 mL of distilled water and 200 mL of methanol in this order in a suction filter and dried in vacuum. The initiator-introduced graphite obtained by these operations was stored in a refrigerator with light shielded.

(2) Graphite Graft Polymerization 0.16 g of sodium heparin (Wako Pure Chemical Industries, Ltd., Osaka, Japan), 0.87 g of trimethylammonium ethyl methacrylate chloride (METMAC) (Sigma-Aldrich Co. LLC), and 1.0 g of acrylamide (Wako Pure Chemical Industries, Ltd., Osaka, Japan) were dissolved in 6 mL of distilled water. Further, 1.0 g of methylenebisacrylamide (MBAA) (Wako Pure Chemical Industries, Ltd., Osaka, Japan) was dissolved in 18 mL of N,N-dimethylformaldehyde (DMF) (Wako Pure Chemical Industries, Ltd., Osaka, Japan). Both the solutions were mixed to prepare a solution for polymerization. In a quartz test tube, 0.6 g of the initiator-introduced graphite was dispersed in the solution for polymerization, and the dispersion was bubbled with nitrogen gas saturated with a mixed solution of distilled water and DMF (volume ratio: 1:3) for 30 minutes with stirring using a magnetic stirrer to remove oxygen. Then, the resultant was irradiated with light from a xenon lamp (Hamamatsu Photonics K.K., LC5, wavelength: 185 nm to 2000 nm) via optical fiber while bubbling and stirring were continued. Then, the graphite particles were suction-filtered and washed with a mixed solution of distilled water and DMF (volume ratio: 1:3), a 1 M aqueous sodium chloride solution, and distilled water in this order and then dried in vacuum. The obtained MIP-immobilized graphite particles were dried in vacuum and stored in a desiccator.

(3) Preparation of Electrode

The graphite in which MIP was immobilized on the surface was mixed with silicone oil (KF-96-300CS; Shin-Etsu Chemical Co., Ltd.) at a weight ratio of 7:3, and the mixture was kneaded in an agate mortar into a paste state.

A tip of a polyether ether ketone tube or a glass tube fitted with a lead was loaded with the MIP-grafted graphite particles prepared in a paste state. Then, the loaded portion was polished with powder paper under pressure to obtain a MIP-immobilized carbon paste electrode.

A SEM image of the surface of the electrode prepared with the conductive particles unmodified with MIP is shown in FIG. 2.

A SEM image of the surface of the electrode prepared with the conductive particles modified with MIP is shown in FIG. 3.

(4) Sensing of Heparin by Electrochemical Approach

To saline or bovine whole blood, 5 mM of potassium ferrocyanide and 0 to 8 units/mL of heparin were added. The relationship between current and a heparin concentration was compared by cyclic voltammetry with the MIP-immobilized carbon paste electrode (the sensor of the present invention) as a working electrode (counter electrode: platinum, reference electrode: silver/silver chloride electrode, potential scan rate: 200 mV/s).

A MW-immobilized electrode produced by the following method was used as a comparative example.

(Production of MW-Immobilized Electrode for Comparison)

An amino group was introduced to the surface of an indium tin oxide (ITO) thin film by heat treatment in a 10 wt % solution of 3-aminopropyltrimethoxysilane in toluene. The amino group introduced in ITO was peptide-bonded to chloromethylbenzoic acid (0.1 M) using water-soluble carbodiimide (0.2 M) in a dimethylformamide solvent to introduce a chloromethylbenzyl group to the ITO surface. The chlorobenzyl group of the ITO surface was reacted in a solution (0.3 M) of sodium diethyldithiocarbamate in ethanol to introduce a diethyldithiocarbamylbenzyl group as a radical polymerization initiator to the ITO surface.

80 mg of sodium heparin as a template, 225 mg of methacryloxyethyltrimethylammonium chloride as a cationic functional monomer, and 250 mg of acrylamide as a monomer for adjustment of the degree of crosslinking were dissolved in 1 mL of water. The aqueous solution was mixed with a solution containing 250 mg of a crosslinkable monomer methylenebisacrylamide dissolved in 3 mL of dimethylformamide. A quartz tube was charged with the mixed solution, and the diethyldithiocarbamylbenzyl group-introduced ITO was dipped therein while irradiated with ultraviolet ray from a germicidal lamp for 24 hours for graft polymerization. Then, the ITO was ultrasonically washed in distilled water. The ITO treated with the solution containing heparin was used as a MIP (molecularly imprinted polymer) electrode.

(Degree of Change in Current Density Ascribable to Change in Heparin Concentration)

FIGS. 4 and 6 show the concentration of heparin and change in the current density when the sensor of the present invention was used (FIG. 4: the relationship between the heparin concentration and the current density, FIG. 6: the relationship between the heparin concentration and the current density in whole blood (bovine blood) and in saline). By contrast, FIGS. 5 and 7 show the concentration of heparin and change in the current density when the sensor prepared by the conventional technique was used (FIG. 5: the relationship between the heparin concentration and the current density, FIG. 7: the relationship between the heparin concentration and the current density in whole blood (bovine blood) and in saline).

When the current density vs. heparin concentration was compared between the sensor of the present invention and the sensor of the conventional technique, the sensor of the present invention was found to have change in the current density as very large as 6000 $\mu A/cm^2$ ascribable to change in the heparin concentration with respect to a range on the order of 200 $\mu A/cm^2$ in the sensor of the conventional technique. As seen from these results, the present invention enables highly sensitive measurement as compared with the conventional sensor.

(Variation in Sensor Performance)

In FIG. 4, a plurality of MIP carbon paste electrodes of the present invention were produced and examined for their heparin concentrations and change in the current density. In FIG. 5, electrodes that permitted current density measurement among MIP-immobilized electrodes prepared by the conventional technique were examined for their heparin concentrations and change in the current density.

As seen from FIGS. 4 and 5, when the sensors of the present invention were compared, all the electrodes of the present invention were measurable electrodes with small variations thereamong (FIG. 4). On the other hand, the conventional electrodes also included electrodes that were unable to exert performance (electrodes C and D), with 20% to 50% variations in performance (FIG. 5).

As seen from these results, the sensor of the present invention enables production of sensors with small variations in performance and enables highly reproducible measurement.

(Comparison of Performance in Aqueous System and Blood System)

FIG. 6 shows the relationship between the heparin concentration and the current density in the aqueous system (saline) and the blood system (whole blood) using the MIP-immobilized carbon paste electrode of the present invention. FIG. 7 shows the heparin concentration and change in the current density in the aqueous system and the blood system using the MIP-immobilized electrode produced by the conventional technique for comparison.

The drawing shows that the MIP-immobilized electrode has large change in the current density ascribable to change in the heparin concentration in the aqueous system, but has small change in the current density and thus cannot exert performance as a sensor in the blood system. On the other hand, the response current of the MW-immobilized carbon paste electrode of the present invention had small difference in sensitivity between the aqueous system and the blood system, showing that the electrode can exert stable performance in both the cases.

Example 2

(1) Graft Polymerization

Vancomycin hydrochloride as a template substance, acrylamide as a monomer for adjustment of the degree of crosslinking, itaconic acid as a functional monomer, and triethylene glycol dimethacrylate (TEDMA) as a crosslinkable monomer were dissolved in a mixed solvent of dimethylformamide (DMF) and water. This solution was used as a polymerization solution. In a quartz tube, initiator-introduced graphite was dispersed in the polymerization solvent, and the dispersion was bubbled with nitrogen gas saturated with a mixed solution of DMF and water (having the same composition as that of the polymerization solvent) for 30 minutes with stirring using a magnetic stirrer to remove dissolved oxygen. Then, the resultant was irradiated with light from a xenon lamp for 3 hours while bubbling and stirring were continued. Then, the graphite particles were suction-filtered and washed with DMF, a 1 M aqueous NaCl solution, and distilled water in this order and then dried in vacuum.

(2) Preparation of Electrode

The graphite in which vancomycin MIP was immobilized on the surface was mixed with silicone oil at a weight ratio of 7:3, and the mixture was kneaded in a PTFE mortar into a paste state. A tip of a hematocrit capillary tube fitted with a lead was loaded with the vancomycin MIP-immobilized graphite particles prepared in a paste state to prepare a vancomycin MIP-immobilized carbon paste electrode.

(3) Electrochemical Sensing

Vancomycin hydrochloride was dissolved at 0 to 1000 μM in an aqueous solution containing 0.1 M sodium chloride and 0.05 M phosphate-buffered salt to prepare a sample. The relationship between current and a concentration was determined by cyclic voltammetry (CV). In this test, 5 mM potassium ferrocyanide was used as a marker substance.

(4) Results

The measurement results are shown in FIG. 8. As shown in FIG. 8, the current value of the vancomycin MIP electrode prepared using TEDMA was increased as the vancomycin concentration was elevated.

Example 3

(1) Graft Polymerization 0.0899 g of vancomycin hydrochloride as a template substance, 0.5002 g of acrylamide as a monomer for adjustment of the degree of crosslinking, 0.5002 g of itaconic acid as a functional monomer, and 2.9781 g of triethylene glycol dimethacrylate (TEDMA) as a crosslinkable monomer were dissolved in a mixed solvent of 24 mL of dimethylformamide (DMF) and 4 mL of water. This solution was used as a polymerization solution. In a quartz tube, 0.6018 g of initiator-introduced graphite was dispersed in the polymerization solvent, and the dispersion was bubbled with nitrogen gas saturated with a mixed solution of DMF and water (having the same composition as that of the polymerization solvent) for 30 minutes with stirring using a magnetic stirrer to remove dissolved oxygen. Then, the resultant was irradiated with light from a xenon lamp for 5.5 hours while bubbling and stirring were continued. Then, the graphite particles were suction-filtered and washed with DMF, a 1 M aqueous NaCl solution, and distilled water in this order and then dried in vacuum.

(2) Preparation of Electrode

The graphite in which MIP for vancomycin was immobilized on the surface was mixed with silicone oil at a weight ratio of 7:3, and the mixture was kneaded in a PTFE mortar into a paste state. A tip of a hematocrit capillary tube fitted with a lead was loaded with the vancomycin MIP-immobilized graphite particles prepared in a paste state to prepare a vancomycin MIP-immobilized carbon paste electrode.

(3) Electrochemical Sensing

Vancomycin hydrochloride was dissolved at 0 to 80 μg/mL in an aqueous solution containing 0.1 M sodium chloride as a supporting electrolyte, 0.05 M phosphate-buffered salt of pH 7.4, and 5 mM potassium ferrocyanide as a redox marker to prepare a sample. The relationship between ferrocyanide ion oxidation current and a vancomycin concentration was determined by cyclic voltammetry (CV) using the vancomycin MIP-immobilized carbon paste electrode.

(4) Results

Change in the peak oxidation current of the ferrocyanide ion ascribable to the vancomycin addition is shown in FIG. 9. The current was elevated with increase in the vancomycin concentration. The dynamic range in which the elevation in the current was seen covered the effective concentration range in blood of vancomycin (10 to 45 μg/mL). This electrode can be expected as a sensor conveniently quantifying the vancomycin concentration.

Example 4

(1) Graft polymerization 0.24 g of sodium warfarin as a template, 0.76 g of metacryloxyethyl as a functional monomer, and 2.5 g of ethylene glycol dimethacrylate as a crosslinkable monomer were dissolved in a mixed solvent of 15 mL of dimethylformamide (DMF) and 5 mL of water. This solution was used as a polymerization solution. In a quartz tube, 0.32 g of initiator-introduced graphite was dispersed in the polymerization solvent, and the dispersion was bubbled with nitrogen gas saturated with a mixed solution of DMF and water (volume ration: 3:1) for 30 minutes with stirring using a magnetic stirrer to remove dissolved oxygen. Then, the resultant was irradiated with light from a xenon lamp for 2 hours while bubbling and stirring were continued. Then, the graphite particles were suction-filtered and washed with a mixed solution of DMF and water at a volume ratio of 3:1, distilled water, a 1 M aqueous NaCl solution, distilled water, and methanol in this order, then dried in vacuum, and stored in a refrigerator with light shielded. This was used as warfarin MIP-immobilized graphite.

(2) Preparation of Electrode

The graphite in which vancomycin MIP was immobilized on the surface was mixed with silicone oil at a weight ratio of 7:3, and the mixture was kneaded in a PTFE mortar into a paste state. A tip of a hematocrit capillary tube fitted with a lead was loaded with the warfarin MIP-immobilized graphite particles prepared in a paste state or non-imprinted polymer graphite particles to prepare a warfarin MIP-immobilized carbon paste electrode or a non-imprinted polymer-immobilized carbon paste electrode.

(3) Electrochemical Sensing

Warfarin was dissolved at 0 to 0.8 μg/mL in an aqueous solution containing 0.1 M sodium chloride as a supporting electrolyte, 0.05 M phosphate-buffered salt of pH 7.4, and 5 mM potassium ferrocyanide as a redox marker to prepare a sample. The relationship between a current and a concentration was determined by CV using the warfarin MIP-immobilized carbon paste electrode or the non-imprinted polymer-immobilized carbon paste electrode.

(4) Results

The relationship between the warfarin concentration and the peak oxidation current of the ferrocyanide ion is shown in FIG. 10. The current was elevated with increase in the vancomycin concentration. The dynamic range in which the elevation in the current was seen covered the effective concentration range in blood of warfarin (10 to 45 µg/mL). This electrode can also be expected as a sensor conveniently quantifying the warfarin concentration.

Reference Example 1: Change in Current Density Ascribable to Change in Heparin Concentration A NIP (non-imprinted polymer)-immobilized carbon paste electrode was produced in the same way as in Example 1 except that the template sodium heparin was not used in the production of the MIP-immobilized carbon paste electrode of Example 1.

The concentration of heparin and change in the current density when the NIP-immobilized carbon paste electrode is used are shown in FIG. 11. The NIP-immobilized carbon paste electrode was confirmed to exhibit no response to heparin.

The relationship between an unfractionated heparin concentration and relative change in the current, and the relationship between a chondroitin C sulfate concentration and relative change in the current in bovine whole blood and in saline are shown in FIG. 12 as to the MIP carbon paste electrode of the present invention produced in Example 1. The MIP carbon paste electrode of the present invention produced in Example 1 was found to have no reaction with chondroitin C sulfate.

Reference Example 2: Contact Angle Measurement of MIP Carbon Paste (MIP-CP) Electrode and NIP Carbon Paste (NIP-CP) Electrode Surface In order to test the hypothesis that the reason why the MIP-CP electrode selectively responds to heparin would be that the reaction of MIP with heparin enhances hydrophilicity so that the oil attached to the MIP is moved backward to increase the effective area of the MIP as an electrode, the contact angle of water with respect to the electrode surface was measured, and change in the hydrophilicity of the electrode surface between before and after addition of heparin was measured.

(1) Experimental Operation (1-1) Preparation of Carbon Paste (CP) Flat-Plate Electrode The MIP-immobilized graphite particles produced in Example 1 were used as MW graphite powders.

MIP-CP (liquid paraffine) was a paste produced by kneading the MIP graphite particles with an oil (liquid paraffine) at a weight ratio of 7:3 for 20 minutes in a mortar.

NIP-CP (liquid paraffine) was a paste produced by kneading graphite particles with an oil (liquid paraffine) at a weight ratio of 7:3 for 20 minutes in a mortar, wherein the graphite particles were produced in the same way as in Example 1 except that the template sodium heparin was not used in the production of the MIP-immobilized graphite particles of Example 1.

As shown in FIG. 13, one PET film (100 µm/film) in which a 4×4 mm hole was opened was layered on already washed ITO glass, and the depression was loaded with the MIP-CP (liquid paraffine), the NIP-CP (liquid paraffine) or the MIP graphite powders. The surface was polished with powder paper.

(1-2) Contact Angle Measurement of Electrode Surface (Before Dipping in Heparin Solution, Saline or Chondroitin C Sulfate (CSC) Solution)

(i) The MIP-CP electrode, the NIP-CP electrode or the electrode loaded with the MIP graphite powders was placed on a sample table, and a syringe was loaded with pure water. The pure water was added dropwise onto the measurement sample at a dropping rate of 4.0 µL/s and in an amount of 20 µL using an automatic contact angle measurement apparatus.

(ii) The contact angle (advancing contact angle) of the liquid droplet was measured using analytical software (SCA20).

(iii) 10 µL of the liquid droplet on the electrode was aspirated at a rate of 4.0 µL/s, and the contact angle (receding contact angle) was measured in the same way as in the operation (ii).

(iv) The liquid droplet was dried with a dryer, and the operations (i) to (iii) were repeated a total of three times using the same electrode.

(v) The electrode was changed, and the number of trials was increased to 3.

(1-3) Dipping of Electrode in Heparin Solution

The electrode was fixed to a cell. A solution of 10 units/mL of heparin, saline or a CSC solution was added into the cell, and the electrode was dipped therein for 10 minutes. Then, the solution remaining on the electrode was blown off with $N_2$ to remove the remaining solution. The electrode was dried using a dryer.

(1-4) Contact Angle Measurement of Electrode Surface (after Dipping in Heparin Solution, Saline or CSC Solution)

The same experiment as in the paragraph (1-2) was conducted.

(2) Results and Discussion (2-1) Contact Angle Measurement of Electrode Loaded with MIP Graphite Powder The contact angle measurement of the electrode loaded with the graphite powders was attempted. However, the liquid droplet penetrated into the MIP graphite powders as shown in FIG. 15. Accordingly, the MIP graphite powders themselves were shown to have very high surface hydrophilicity.

(2-2) Contact Angle Measurement of MIP-CP Electrode (Heparin Solution)

The contact angle of the MIP-CP electrode was measured. The contact angles before and after the dipping in the heparin solution were as described below. The contact angle is defined as an average value of the right and left contact angles. As shown in FIG. 16, the hydrophilicity of the MIP-CP electrode was found to be enhanced by the dipping in the heparin solution. The rate of change in the advancing contact angle was −18%, and the rate of change in the receding contact angle was −23%.

Change in the hydrophilicity was also confirmable visually (FIGS. 17 and 18).

(2-3) Contact Angle Measurement of MIP-CP Electrode (Saline)

The heparin solution was a solution containing sodium heparin dissolved in saline. In order to examine no involvement of saline in the change in the hydrophilicity shown here, the MIP-CP electrode was dipped in saline and evaluated for its hydrophilicity before and after the dipping. FIG. 19 shows change in the hydrophilicity of the sensor between before and after the dipping in the saline. The rate of change in the advancing contact angle was 0.2%, and the rate of change in the receding contact angle was 3%. Accordingly, it was suggested that the saline has no influence on the hydrophilicity of the electrode.

(2-4) Contact Angle Measurement of MIP-CP Electrode (CSC Solution)

The electrode was dipped in the CSC solution and examined for change in the hydrophilicity between before and after the dipping. CSC (chondroitin C sulfate) is an analog of heparin. If the dipping of the electrode in the CSC solution causes no change in the hydrophilicity, it is suggested that MIP selectively responds to heparin. FIG. 20 is a graph summarizing the contact angles before and after the dipping in the CSC solution. The rate of change in the advancing contact angle was −2%, and the rate of change in the receding contact angle was 5%. Accordingly, it was suggested that MIP selectively responds to heparin.

(2-5) Contact Angle Measurement of NIP-CP Electrode (Heparin Solution)

The NIP-CP electrode was examined for change in the hydrophilicity between before and after the dipping in the heparin solution. The involvement of MIP in change in the hydrophilicity is determined by comparing the change in the hydrophilicity of the NIP-CP electrode between before and after the dipping in the heparin solution with that of the MIP-CP electrode. FIG. 21 shows change in the hydrophilicity of the NIP-CP electrode between before and after the dipping in the heparin solution. The rate of change in the advancing contact angle was −0.3%, and the rate of change in the receding contact angle was −5%. Accordingly, it was suggested that MIP is involved in the change in the hydrophilicity caused by the dipping of the electrode in the heparin solution.

(2-6) Summary of Contact Angle of Each Electrode

The respective results were compared. The results about the advancing contact angle are shown in FIG. 22. The hydrophilicity of the MIP-CP electrode varied largely only under conditions of dipping in the heparin solution.

TABLE 1

| | Rate of change in advancing contact angle | | | |
|---|---|---|---|---|
| | MIP-CP electrode (Heparin solution) | NIP-CP electrode (Heparin solution) | MIP-CP electrode (Saline) | MIP-CP electrode (CSC SOLUTION) |
| Rate of change [%] | −18 | −0.3 | 0.2 | −2 |

The results about the receding contact angle are shown in FIG. 23. As for the receding contact angle, the hydrophilicity of the MIP-CP electrode also varied largely only under conditions of dipping in the heparin solution.
[Table 2]

TABLE 2

| | Rate of change in receding contact angle | | | |
|---|---|---|---|---|
| | MIP-CP electrode (Heparin solution) | NIP-CP electrode (Heparin solution) | MIP-CP electrode (Saline) | MIP-CP electrode (CSC SOLUTION) |
| Rate of change [%] | −23 | −5 | 3 | 5 |

The results described above demonstrated that the reason why the MIP-CP electrode selectively responds to heparin is that the reaction of MIP with heparin enhances hydrophilicity so that the oil attached to the MIP is moved backward to increase the effective area of the MIP as an electrode

The invention claimed is:

1. A paste sensor comprising:
    a conductive particle having a molecularly imprinted polymer on the surface;
    an oil binder for the conductive particle; and
    a support,
    wherein the conductive particle is a spherical graphite particle having a diameter of 3-50 μm,
    wherein the conductive particle having a molecularly imprinted polymer on the surface is a conductive particle obtained by polymerizing a functional monomer, a crosslinkable monomer, and a measurement substance through contact with a graphite particle wherein an initiator was immobilized on surface of the graphite particle, and
    wherein the sensor is configured to selectively respond to the measurement substance in that the molecularly imprinted polymer is structured such that when the molecularly imprinted polymer is reacted with the measurement substance, hydrophilicity of the molecularly imprinted polymer is enhanced in an amount effective such that the oil binder attached to the molecularly imprinted polymer is moved backward to increase the effective area of the molecularly imprinted polymer as an electrode, and as a result the sensor can selectively respond to the measurement substance.

2. The sensor according to claim 1, wherein the functional monomer is a cationic monomer.

3. The sensor according to claim 1, wherein the functional monomer is trimethylammonium ethyl methacrylate chloride.

4. The sensor according to claim 1, wherein the crosslinkable monomer is methylenebisacrylamide.

5. The sensor according to claim 1, wherein for the polymerization, a monomer for adjustment of the degree of crosslinking is further contacted with a substrate.

6. The sensor according to claim 5, wherein the monomer for adjustment of the degree of crosslinking is acrylamide.

7. The sensor according to claim 1, wherein the measurement substance is a hormone, an antimicrobial agent, or an anticoagulant.

8. The sensor according to claim 1, wherein the measurement substance is heparins, warfarin, serotonin, or vancomycin.

9. A method for measuring a measurement substance, comprising:

contacting a sample containing the measurement substance with a sensor according to claim 1; and
detecting change in signal.

10. The method for measuring a measurement substance according to claim 9, further comprising detecting change in current as the change in signal.

11. The measurement method according to claim 9, wherein the sample is whole blood or a blood component.

12. The sensor according to claim 1, wherein the initiator is immobilized directly on the surface of the graphite particle.

13. The sensor according to claim 1, wherein the initiator is immobilized directly on the surface of the graphite particle via a covalent bond.

\* \* \* \* \*